United States Patent [19]

Richards

[11]  4,271,154
[45]  Jun. 2, 1981

[54] OINTMENT FOR TREATMENT OF ARTHRITIS

[76] Inventor: Levie Richards, R.D. 2, Box 126, Whitehouse Station, N.J. 08889

[21] Appl. No.: 940,988

[22] Filed: Sep. 11, 1978

[51] Int. Cl.³ .............................................. A61K 35/78
[52] U.S. Cl. .................................................... 424/195
[58] Field of Search ................................ 424/196, 195

[56] References Cited

FOREIGN PATENT DOCUMENTS 3909 of 1910 United Kingdom ...................... 424/195

Primary Examiner—Stanley J. Friedman

[57] ABSTRACT

The present application relates to the treatment of arthritis and related disorders and to a particular composition suitable thereto. The composition comprises a mixture of white petroleum jelly and the reaction products of lead-free gasoline in combination with dried and ground pods or seeds of the capsicum plants mixed to form an ointment to application to the affected part of the body.

7 Claims, No Drawings

OINTMENT FOR TREATMENT OF ARTHRITIS

This application is a substitute for my previous U.S. application, Ser. No. 44,873 filed Mar. 6, 1974, now abandoned.

The present invention relates to a composition of matter and to a method of making an ointment for the treatment of arthritis. The composition comprises an admixture of white petroleum jelly and the reaction product of lead-free gasoline with vegetable products derived from the seed and pods of the capsicum plant commonly known as red pepper. In particular this invention concerns on ointment particularly useful in the treatment of arthritis and related diseases as they occur in humans, lower primates and other animals. The ointment may be utilized for the temporary relief of aches and pains resulting from arthritis. The ointment is devised for external application to the affected area of the body by applying to the area adjacent to the joint and rubbing it into the skin to alleviate the aches and pains of the disease.

BACKGROUND OF THE INVENTION

Arthritis is medically termed as an inflamation of a joint or joints and is one of a number of diseases and disorders of the skeleton and body system commonly called rheumatism. It arises from many causes, some well-defined, some still unknown, and it is treated in many different ways. There are two common types know as rheumatoid arthritis and degenerative arthritis. The former is a disease not of the joints alone but of the whole bodily system, in particular, the connective body tissue. The latter is a chronic joint disease of age, rarely occurring before the age of 40 in humans. In both cases the manifestations are the same. The joints in the hands, feet and legs are affected. For example, they become swollen and gnarled, so that the digits tend to slant away to the outside. In severe cases unused muscles surrouding the affected area become painful and swollen and joints may become atrophied through non-use.

Various new and old drugs have been developed for the treatment of arthritis, such as cortisone, acth and others, but most have dangerous side effects. Their dosage must be carefully prescribed and administered under controlled conditions and circumstances to avoid very unpleasant side effects. Also, several ointments and liniments have been utilized for the relief of pains and aches of arthritis. Most of these have provided little relief to persons suffering from arthritis.

I have discovered an ointment that can be topically applied to the skin that will bring early relief from the aches and pains of arthritis, reduce the swelling of joints and thereby permit joint and muscular movements that were previously difficult and painful and in some cases impossible.

The ointment is prepared by mixing the following ingredients in these proportions:
1. ½ pint of lead-free gasoline
2. 1¾ ounces of ground red pepper
3. 1 pound of petroleum jelly.

The ingredients are throughly blended by agitating in a mechanical mixing devise to form a semi-solid composition.

In the preferred embodiment of the discovery I used a purified semi-solid mixture of petroleum jelly. The petroleum is admixed with ground red pepper derived from dried seeds and pods of the capsicum plant. To this mixture a distilled hydrocarbon product, commonly referred to as lead-free gasoline is added.

It is believed that it is the reaction product which is important to my discovery only and that ideally this product, if isolated and contained in the petroleum base may yet prove to be the commercially feasible ointment. However, it has been proven to be difficult to separate or distill this product from the non-reacting constituent parts.

QUALITATIVE INFRA RED SPECTROSCOPE AND OTHER TESTS

The following results were obtained from making intimate admixtures of two of the ingredients at a time, of the three ingredients of the ointment.

EXAMPLE 1

The intimate admixture of white petroleum jelly and ground red pepper produced a new chemical bonding and associations. A new H-bonded hydroxyl, not present in either of the ingredients alone, was produced as evidenced by the infra red absorption at 3200 CM-1. A new sharp band at 1647 CM-1 indicated a change in an amide grouping present in the red pepper component. A new 1027 CM-1 band indicated a change in a primary alcohol grouping of a red pepper component.

EXAMPLE 2

The intimate admixture of white petroleum jelly and unleaded or lead-free gasoline produced an unexpected new chemical bondings and groupings. Bands at 1167 and 1155 CM-1 indicated a change in an isopropyl type grouping brought about by the admixture. New resolved bands at 917 and 874 CM-1 indicate new chemical groupings which could be substituted cyclobutanes.

EXAMPLE 3

The intimate admixture of unleaded or lead-free gasoline and ground red pepper gave rise to new and changed chemical bondings. Different infra red absorptions at 1168 and 1156 CM-1 indicated a change in an isopropyl type grouping brought about by reaction between the gasoline and red pepper. Also, the same conclusion applied to the different 1143 CM-1 band, new resolved bands at 905 and 876 CM-1 suggested a change in skeletal C—C structure which could arise from a change in substituted cyclobutanes.

Results of all tests detailed in examples 1, 2, and 3 shown above, conducted by Kendall Infra red Laboratories, Plainfield, N.J., show that all three of the ingredients of my arthritis ointment formulation contributed new and unexpected chemical components by reaction with each other. This formulation is believed to produce a series of new components and new chemical groupings brought about by chemical reactions among the ingredients.

Kendall Infra red Laboratories also made tests on a sample mixture of the three ingredients of the ointment in combination. It was evidenced by this test that new components were formed by the preparation. It was found that new bands at 1072 and 1034 CM-1 were formed which were not present in the individual components and particularly stronger than those in the red pepper. Also, in the ointment of my invention the hydroxyl absorption was at 3289 CM-1 as compared to 3333 CM in the red pepper, which is considered to be the only ingredient contributing sustantial hydroxyl moreties to the final product. Further, it was found that 1715 carbonyl absorption band of the ointment changed from the 1718 CM-1 carbonyl absorption of red pepper alone.

ACTUAL TESTS

My ointment has been used on humans as well as animals with satisfactory results in most cases:

Case 1

A horse suffering from a navicular ring bone was treated with a known chemical compound identified as palacine. The animal failed to show any improvement. However, after application of my ointment, the horse has in every since appeared to be cured of that ailment.

Case 2

A horse suffering from arthritis was treated with cortisone to relieve the crippling of that malady. The treatment failed, but after an application of my ointment the horse was greatly relieved and has since showed not signs of the effects of arthritis.

Skin tests have been run by the Berke Laboratories, Roselle Park, N.J. at my direction to determine the effects of my ointment may have on body and animal organs. All of these tests were negative and thus the ointment has not proven to have any harmful side effects.

The invention has been described in an illustrative manner, and it is to be understood that the terminology which has been used is intended to be in the nature of description rather than limitation.

Obviously, many modifications and variations of the present invention was possible in light of the above teachings. It is therefore to be understood that within the scope of the appended claims, the invention may be practiced otherwise than as specifically described.

The embodiment of the invention in which an exclusive property or privilege is claimed is defined as follows:

1. A method for producing a composition of reacted ingredients, comprising in combination: admixing petroleum jelly with red pepper sufficiently and for an interval of time sufficient to obtain a first composition characterized by infra-red analysis indicative of infra-red absorption at 3200 CM-1 and a sharp band at 1647 CM-1 and a new band at 1027 CM-1, and thereafter admixing therewith a lead-free gasoline with said first composition sufficiently to obtain a semi-solid ointment characterized by infra-red analysis indicative of new bands at 1072 and 1034 CM-1 not present in individual components and more intense than bands in red pepper analysis, and further indicative of hydroxyl absorption at 3289 CM-1 and a carbonyl absorption band at 1715 CM-1.

2. A method for producing a composition of reacted ingredients, comprising in combination: admixing petroleum jelly with red pepper and with lead-free gasoline sufficiently and for an interval of time sufficient for reaction to take place to thereby form a semi-solid ointment characterized by infra-red analysis indicative of new bands at 1072 and 1034 CM-1 not present in individual components and more intense than bands in red pepper analysis, and further indicative of hydroxyl absorption at 3289 CM-1 and a carbonyl absorption band at 1715 CM-1.

3. A composition of matter consisting essentially of red pepper, petroleum jelly and lead-free gasoline, produced by admixing the same in proportions and for a time interval sufficient to form a semi-solid ointment characterized by infra-red analysis indicative of new bands at 1072 and 1034 CM-1 not present in individual components and more intense than bands in red pepper analysis, and further indicative of hydroxyl absorption at 3289 CM-1 and a carbonyl absorption band at 1715 CM-1.

4. A composition of matter of claim 3, in which said petroleum jelly is white petroleum jelly, and in which said red pepper is dried red pepper derived from dried seeds and pods of capsium plant particulated into particulated red pepper prior to said mixing and comprises particulated red pepper.

5. A composition of matter consisting essentially of red pepper, petroleum jelly and lead-free gasoline, produced by admixing the same in relative proportions of substantially about ½ pint of said lead-free gasoline to one pound (U.S.) of said petroleum jelly and about one and three-fourths dry ounces of said red pepper, said admixing being sufficient to form a semi-solid ointment characterized by infra-red analysis indicative of new bands at 1072 and 1034 CM-1 not present in individual components and more intense than bands in red pepper analysis, and further indicative of hydroxyl absorption at 3289 CM-1 and a carbonyl absorption band at 1715 CM-1.

6. A composition of matter of claim 5, in which said admixing comprises first admixing together said petroleum jelly and said red pepper in particulated form, followed by thereafter adding said lead-free gasoline thereto and admixing therewith.

7. A composition of matter consisting of a semi-solid ointment produced by particulating red pepper derived from dried seeds and pods of capsium plant to obtain particulated red pepper, and thereafter admixing the particulated red pepper with white petroleum jelly and with lead-free gasoline in relative proportions of substantially about ½ pint of said lead-free gasoline to one pound (U.S.) of said petroleum jelly and about one and three-fourths dry ounces of said particulated red pepper.

* * * * *